(12) United States Patent
Mikami et al.

(10) Patent No.: US 8,859,789 B2
(45) Date of Patent: Oct. 14, 2014

(54) METHOD FOR PRODUCING OPTICALLY ACTIVE FLUORINE-CONTAINING OXETEN

(75) Inventors: Koichi Mikami, Tokyo (JP); Kohsuke Aikawa, Tokyo (JP); Yuta Hioki, Tokyo (JP)

(73) Assignee: Tokyo Institute of Technology, Tokyo (JP)

( * ) Notice: Subject to any disclaimer, the term of this patent is extended or adjusted under 35 U.S.C. 154(b) by 0 days.

(21) Appl. No.: 13/989,662

(22) PCT Filed: Nov. 16, 2011

(86) PCT No.: PCT/JP2011/076359
§ 371 (c)(1),
(2), (4) Date: Jul. 29, 2013

(87) PCT Pub. No.: WO2012/070437
PCT Pub. Date: May 31, 2012

(65) Prior Publication Data
US 2013/0310580 A1    Nov. 21, 2013

(30) Foreign Application Priority Data
Nov. 26, 2010  (JP) ................ 2010-263128

(51) Int. Cl.
C07D 407/00  (2006.01)
C07D 305/10  (2006.01)
C07D 407/04  (2006.01)
C07D 409/04  (2006.01)

(52) U.S. Cl.
CPC ............ *C07D 305/10* (2013.01); *C07D 407/04* (2013.01); *C07D 409/04* (2013.01)
USPC ....................................... 549/511

(58) Field of Classification Search
CPC .................................................. C07D 305/10
USPC ....................................... 549/511
See application file for complete search history.

(56) References Cited

U.S. PATENT DOCUMENTS

2011/0306781 A1   12/2011  Mikami et al.

FOREIGN PATENT DOCUMENTS

JP    2010-195736 A    9/2010
JP    2010-222345 A    10/2010

OTHER PUBLICATIONS

Chinese Office Action dated Mar. 28, 2013 (eight (8) pages).
Corresponding International Search Report with English Translation dated Feb. 14, 2012 (five (5) pages).
Japanese-language Written Opinion dated Feb. 14, 2012 (PCT/ISA/237) (three (3) pages).
Alexander S. Golubev et al., "Carbonyl-yne Reactions of 3,3,3-Trifluoropyruvates", Science Direct, Tetrahedron, vol. 59, No. 9, 2003, pp. 1389-1394.
Theodora W. Greene et al., "Protective Groups in Organic Synthesis", John Wiley & Sons, Inc., 3rd edition, 1999, (fifty-five (55) pages).
Iwao Ojima, "Catalytic Asymmetric Synthesis", Wiley-VCH, Inc., $2^d$ edition, 2000, pp. 34-83.
Kohsuke Aikawa et al., "Asymmetric Catalysis of ene Reactions with Trifluoropyruvate Catalyzed by Dicationic Palladium(II) Complexes", Science Direct, Tetrahedron Letters, vol. 45, 2004, pp. 183-185.
Koichi Mikami et al., Enantioselective Catalysis of Carbonyl-ene and Friedel-Crafts Reactions with Trifluoropyruvate by Naked Palladium(II) Complexes with Segphos Ligands, Science Direct, Tetrahedron Asymmetry, vol. 15, 2004, pp. 3885-3889.
Koichi Mikami et al., "Enantiodiscrimination and Enantiocontrol of Neutral and Cationic $Pt^{II}$ Complexes Bearing the Tropos Biphep Ligand: Application to Asymmetric Lewis Acid Catalysis", Angew. Chem. Int. Ed., vol. 44, 2005, pp. 7257-7260.
Simon Doherty et al., "Asymmetric Platinum Group Metal-Catalyzed Carbonyl-Ene Reactions: Carbon-Carbon Bond Formation Versus Isomerization", J. Org. Chem., vol. 71, 2006, pp. 9751-9764.
David A. Evans et al., "C2-Symmetric Copper(II) Complexes as Chiral Lewis Acids. Scope and Mechanism of the Catalytic Enantioselective Aldol Additions of Enolsilanes to Pyruvate Esters", J. Am. Chem., Soc., vol. 121, 1999, pp. 686-699.
Koichi Mikami et al., "Asymmetric Synthesis by Enantiomer-Selective Activation of Racemic Catalysts", Nature, vol. 385, 1997, pp. 613-615.
Guenther Maier et al., "Reaktionen von Tetra-tert-butyltetrahedran: Oxidation zum Radikal-Kation als einleitender Schritt", Liebigs Ann. , No. 1, 1995, pp. 161-167.
Magali Oblin et al., "Experimental Evidence for a [2+2] Mechanism in the Lewis Acid-Promoted Formation of a,fβ-unsaturated Esters from Ethoxyacetylene and Aldehydes. Synthesis and Characterisation of 4-ethoxyoxetes", Chem. Commun., No. 16, 1998, pp. 1619-1620.
M. Longchar et al., "A Convenient Synthesis of Oxetene Via [2+2]Cycloaddition Reaction Under Microwave Irradiation", Synthetic Communications, vol. 32, No. 23, 2002, pp. 3611-3616.
Akio Hayashi et al., "SbF 5-Promoted Addition of Aldehydes to Alkynes", Synlett, 1995, pp. 195-196.
W. J. Middleton, "The Isolation of a Cyclic Intermediate in the Ketone-Alkoxyacetylene Reaction", Journal of Organic Chemistry, vol. 30, No. 4, 1965, p. 1307.
Louis E. Friedrich et al., "Detection of an Oxetene Intermediate in the Photoreaction of Benzaldehyde with 2-Butyne", Journal of the American Chemical Society, vol. 95, No. 20, 1973, pp. 6869-6870.
Louis E. Friedrich et al, "Photochemical Preparation of a Stable Oxetene", Journal of the American Chemical Society, vol. 91, No. 25, 1969, pp. 7204-7205.
Louis E. Friedrich et al., "Synthesis and Reactions of 3-Phenyloxete and the Parent Unsubstituted Oxete", J. Org. Chem., vol. 46, No. 2, 1981, pp. 306-311.
Waldemar Adam et al., "Dimethyldioxirane Epoxidation of Benzofurans: Reversible Thermal and Photochemical Valence Isomerization Between Benzofuran Epoxides, Quinone Methides, and Benzoxetenes", J. Am. Chem. Soc., vol. 115, No. 19, 1993, pp. 8603-8608.

*Primary Examiner* — Andrew D Kosar
*Assistant Examiner* — Raymond Covington
(74) *Attorney, Agent, or Firm* — Crowell & Moring LLP

(57) ABSTRACT

A method for producing an optically active fluorine-containing oxeten, the method being provided to include the steps of causing a fluorine-containing α-ketoester and an internal alkyne to react with each other in the presence of a transition metal complex that has an optically active ligand.

5 Claims, No Drawings

METHOD FOR PRODUCING OPTICALLY ACTIVE FLUORINE-CONTAINING OXETEN

TECHNICAL FIELD

The present invention relates to a method for producing an optically active fluorine-containing oxeten and the like.

BACKGROUND OF THE INVENTION

An optically active fluorine-containing oxeten, the target of the present invention, is a compound that can be an important intermediate for pharmaceuticals and agrochemicals.

As a conventional technique, there has been reported a [2+2] cycloaddition reaction between methyl trifluoropyruvate and ethoxyacetylene (Non-Patent Publication 1).

Additionally, there is also known a method of causing hydrolysis after reacting a fluorine-containing α-ketoester with silylacetylene in the presence of "a transition metal complex that has an optically active ligand" thereby producing a product that can become an optically active fluorine-containing alkynyl (Patent Publication 1).

Furthermore, there is also known a method of causing a fluorine-containing α-ketoester and an acyl alkenyl ether to react with each other in the presence of "a transition metal complex that has an optically active ligand" thereby producing an optically active fluorine-containing oxetane (Patent Publication 2).

REFERENCES ABOUT PRIOR ART

Patent Publication

Patent Publication 1: Japanese Patent Application Publication No. 2010-195736
Patent Publication 2: Japanese Patent Application Publication No. 2010-222345

Non-Patent Publication

Non-Patent Publication 1: Tetrahedron (England), 2003, Vol. 59, No. 9, p. 1389-1394

SUMMARY OF THE INVENTION

Problems to be Solved by the Invention

An optically active fluorine-containing oxeten, the target of the present invention, is a novel compound and there has been known no production method relating to the oxeten.

In Non-Patent Publication 1, a fluorine-containing oxeten is only supposed to be present as a reaction intermediate, and actually, the oxeten is not able to be isolated because of its unstability. Moreover, Non-Patent Publication) does not assume the production of an optically active compound.

In Patent Publications 1 and 2, silylacetylene and acyl alkenyl ether are used as a nucleophile; however, in the present invention an internal alkyne different from these is used.

Also concerning products to be obtained, these are different evidently in structure (a product that can become an optically active fluorine-containing alkynyl, an optically active fluorine-containing oxetane vs. an optically active fluorine-containing oxeten).

Additionally, it is known that a carbonyl-ene reaction is caused in an alkyne having a hydrogen atom at a propargyl moiety. An internal alkyne used in the present invention also contains such an alkyne and therefore bears a concern about 2,3-allenol formed as a by-product.

Under the circumstances, it has been desired to develop a practical production method by which an optically active fluorine-containing oxeten which can become an important intermediate for pharmaceuticals and agrochemicals is able to be stably isolated.

Means for Solving the Problems

The present invention is an invention achieved in view of the above circumstances to provide the following method for producing an optically active fluorine-containing oxeten, and more specifically to provide [Invention 1] to [Invention 5].

[Invention 1]

A method for producing an optically active fluorine-containing oxeten represented by general formula [3], comprising the steps of:

causing a fluorine-containing α-ketoester represented by general formula [1] and an internal alkyne represented by general formula [2] to react with each other in the presence of a transition metal complex that has an optically active ligand.

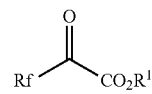

[1]

[In the formula [1], Rf represents a perfluoroalkyl group and $R^1$ represents an alkyl group.]

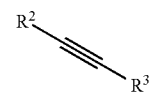

[2]

[In the formula [2], $R^2$ and $R^3$ mutually independently represent a halogen atom, an alkyl group, a substituted alkyl group, an aromatic cyclic group, a substituted aromatic cyclic group, a nucleobase, a substituted nucleobase, an alkoxycarbonyl group or a substituted alkoxycarbonyl group.]

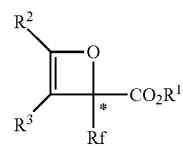

[3]

[In the formula [3], Rf, $R^1$, $R^2$ and $R^3$ represent the same substituents as the above and "*" represents an asymmetric carbon.]

[Invention 2]

A method for producing an optically active fluorine-containing oxeten represented by general formula [6], comprising the steps of:

causing a fluorine-containing α-ketoester represented by general formula [4] and an internal alkyne represented by general formula [5] to react with each other in the presence of a divalent cationic transition metal complex that has an optically active ligand.

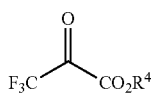

[In the formula [4], $R^4$ represents a methyl group or an ethyl group.]

[In the formula [5], $R^5$ represents an aromatic cyclic group, a substituted aromatic cyclic group, a nucleobase or a substituted nucleobase, and $R^6$ represents a halogen atom, an alkyl group, a substituted alkyl group, an aromatic cyclic group, a substituted aromatic cyclic group, a nucleobase, a substituted nucleobase, an alkoxycarbonyl group or a substituted alkoxycarbonyl group.]

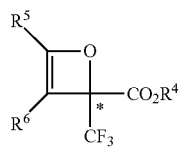

[In the formula [6], $R^4$, $R^5$ and $R^6$ represent the same substituents as the above and "*" represents an asymmetric carbon.]

[Invention 3]

A method as discussed in Invention 1 or 2, characterized in that the transition metal complex that has an optically active ligand is a divalent cationic palladium complex that has an optically active ligand.

[Invention 4]

An optically active fluorine-containing oxeten represented by general formula [3].

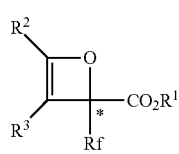

[In the formula [3], Rf represents a perfluoroalkyl group, $R^1$ represents an alkyl group, $R^2$ and $R^3$ mutually independently represent a halogen atom, an alkyl group, a substituted alkyl group, an aromatic cyclic group, a substituted aromatic cyclic group, a nucleobase, a substituted nucleobase, an alkoxycarbonyl group or a substituted alkoxycarbonyl group, and "*" represents an asymmetric carbon.]

[Invention 5]

An optically active fluorine-containing oxeten represented by general formula [6].

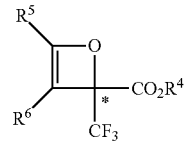

[In the formula [6], $R^4$ represents a methyl group or an ethyl group, $R^5$ represents an aromatic cyclic group, a substituted aromatic cyclic group, a nucleobase or a substituted nucleobase, $R^6$ represents a halogen atom, an alkyl group, a substituted alkyl group, an aromatic cyclic group, a substituted aromatic cyclic group, a nucleobase, a substituted nucleobase, an alkoxycarbonyl group or a substituted alkoxycarbonyl group, and "*" represents an asymmetric carbon.]

Effects of the Invention

According to the present invention, it becomes possible to provide a method for producing an oxeten, the method being able to stably isolate an optically active fluorine-containing oxeten that behaves as a novel compound.

By adopting the production method of the present invention, an optically active fluorine-containing oxeten can be obtained with high regioselectivity and high stereoselectivity (high optical purity) with high yield even in cases where the amount of an asymmetric catalyst is relatively low.

In addition, the thus-obtained optically active fluorine-containing oxeten can also be converted into various useful intermediates.

Thus, the present invention can provide a practical method for producing an optically active fluorine-containing oxeten which can be an important intermediate for pharmaceuticals and agrochemicals.

MODE(S) FOR CARRYING OUT THE INVENTION

Hereinafter, a method for producing an optically active fluorine-containing oxeten according to the present invention and the like will be described in detail. The scope of the present invention may never be limited by the description, and modifications into the other than the following examples may suitably occur within a range not to affect the scope of the present invention. Incidentally, general formulas [1] to [6] discussed below are the same as discussed above.

"Rf" of a fluorine-containing α-ketoester represented by general formula [1] means a perfluoroalkyl group. It is possible to cite $C_1$-$C_{12}$ perfluoroalkyl groups, in which those having a carbon number of three or more can take a straight-chain, branched or cyclic structure.

$R^1$ of a fluorine-containing α-ketoester represented by general formula [1] means an alkyl group. It is possible to cite $C_1$-$C_{12}$ alkyl groups, in which those having a carbon number of three or more can take a straight-chain, branched or cyclic structure.

Of fluorine-containing α-ketoesters, those available on a large scale and having a trifluoromethyl group as a perfluoroalkyl group (Rf) and having a methyl group or an ethyl group as an alkyl group ($R^1$) of the ester moiety are preferable (and more specifically, fluorine-containing α-ketoesters represented by general formula [4] are preferable) for producing an optically active fluorine-containing oxeten.

The amount of the fluorine-containing α-ketoester to be used is required only to be 0.2 mol or more, preferably 0.3 to 7 mol, and particularly preferably 0.4 to 5 mol relative to 1 mol of an internal alkyne represented by general formula [2].

$R^2$ and $R^3$ in the internal alkyne represented by general formula [2] mutually independently represent a halogen atom, an alkyl group, a substituted alkyl group, an aromatic cyclic group, a substituted aromatic cyclic group, a nucleobase, a substituted nucleobase, an alkoxycarbonyl group or a substituted alkoxycarbonyl group.

As a halogen atom, it is possible to cite a fluorine atom, a chlorine atom, a bromine atom and an iodine atom.

As an alkyl group, it is possible to cite $C_1$-$C_{12}$ alkyl groups, in which those having a carbon number of three or more can take a straight-chain, branched or cyclic structure.

As an aromatic cyclic group, it is possible to cite: $C_1$-$C_{18}$ aromatic hydrocarbon groups such as a phenyl group, a naphthyl group, an anthryl group and the like; and aromatic heterocyclic groups having a hetero atom such as a nitrogen atom, an oxygen atom, a sulfur atom and the like, e.g., a pyrrolyl group (a group protected with nitrogen), a pyridyl group, a furyl group, a thienyl group, an indolyl group (a group protected with nitrogen), a quinolyl group, a benzofuryl group, a benzothienyl group and the like.

As a nucleobase, it is possible to cite an adenine residue, a guanine residue, a hypoxanthine residue, a xanthine residue, a uracil residue, a thymine residue, a cytosine residue and the like.

The nucleobase can be protected with a protective group generally used in the field of synthesis of compounds relating to nucleic acid. [For example, a protective group for a hydroxyl group (serving as a functional group after isomerization) can be exemplified by: an acyl group such as an acetyl group, a benzoyl group and the like; an alkyl group such as a methoxymethyl group, an allyl group and the like; an aralkyl group such as a benzyl group, a triphenylmethyl group and the like; and so on. Additionally, a protective group for an amino group can be exemplified by: an acyl group such as an acetyl group, a benzoyl group and the like; an aralkyl group such as a benzyl group; and so on. Furthermore, these protective groups may be substituted with a halogen atom, a lower alkyl group, a lower alkoxyl group or the like.]

Moreover, it is also possible to substitute an amino group and/or a hydroxyl group in the nucleobase with a hydrogen atom, a cyano group, an amino group, an azide group, a nitro group, a hydroxyl group, a halogen atom, a thiol group or the like.

An alkyl moiety (R) of an alkoxycarbonyl group ($CO_2R$) can be exemplified by the alkyl group same as the above.

A substituted alkyl group, a substituted aromatic cyclic group, a substituted nucleobase and a substituted alkoxycarbonyl group are obtained by substituting an arbitrary number and an arbitrary combination of hydrogen atoms on any of a carbon atom, a nitrogen atom, an oxygen atom and/or a sulfur atom of an alkyl group, an aromatic cyclic group, a nucleobase and an alkoxylcarbonyl group with the following substituent.

As the above-mentioned substituent, it is possible to cite: a halogen atom including fluorine, chlorine, bromine and iodine; an azide group; a nitro group; a lower alkyl group such as a methyl group, an ethyl group, a propyl group and the like; a lower haloalkyl group such as a fluoromethyl group, a chloromethyl group, a bromomethyl group and the like; a lower alkoxyl group such as a methoxy group, an ethoxy group, a propoxy group and the like; a lower haloalkoxy group such as a fluoromethoxy group, a chloromethoxy group, a bromomethoxy group and the like; a lower alkylamino group such as a dimethylamino group, a diethylamino group, a dipropylamino group and the like; a lower alkylthio group such as methylthio group, an ethylthio group, a propylthio group and the like; a cyano group; a lower alkoxycarbonyl group such as a methoxycarbonyl group, an ethoxycarbonyl group, a propoxycarbonyl group and the like; a lower alkylaminocarbonyl group such as an aminocarbonyl group, a dimethylaminocarbonyl group, a diethylaminocarbonyl group, a dipropylaminocarbonyl group and the like; an unsaturated group such as a lower alkenyl group (where one hydrogen atom is removed from each of adjacent two carbon atoms of a lower alkyl group (a total number of the hydrogen atoms is two) thereby forming a double bond), a lower alkynyl group (where two hydrogen atoms are removed from each of adjacent two carbon atoms of a lower alkyl group (a total number of the hydrogen atoms is four) thereby forming a triple bond) and the like; an aromatic cyclic group such as a phenyl group, a naphthyl group, a pyrrolyl group, a furyl group, a thienyl group and the like; an aromatic cyclic oxy group such as a phenoxy group, a naphthoxy group, a pyrrolyloxy group, a furyloxy group, a thienyloxy group and the like; an aliphatic heterocyclic group such as a piperidyl group, a piperidino group, a morpholinyl group and the like; a hydroxyl group and a protected hydroxyl group; an amino group (including amino acid and peptide residue) and a protected amino group; a thiol group and a protected thiol group; an aldehyde group and a protected aldehyde group; a carboxyl group and a protected carboxyl group; and the like.

Of these substituents, "the unsaturated group", "the aromatic cyclic group", "the aromatic cyclic oxy group" and "the aliphatic heterocyclic group" may be substituted with a halogen atom, an azide group, a nitro group, a lower alkyl group, a lower haloalkyl group, a lower alkoxy group, a lower haloalkoxy group, a lower alkylamino group, a lower alkylthio group, a cyano group, a lower alkoxycarbonyl group, an aminocarbonyl group, a lower alkylaminocarbonyl group, a hydroxyl group, a protected hydroxyl group, an amino group, a protected amino group, a thiol group, a protected thiol group, an aldehyde group, a protected aldehyde group, a carboxyl group, a protected carboxyl group or the like.

Of these, some substituents relate to a side reaction; however, it is possible to conduct a desired reaction in a good state by adopting suitable reaction conditions.

Incidentally, in this specification, each of the following terms is used as having the following meaning. "Lower" means a straight or branched chain or cyclic chain (with a carbon number of not smaller than 3) having a carbon number of from 1 to 6. In the case that "unsaturated group" is the double bond (i.e., the case of alkenyl group), it may take either E configuration or Z configuration or both.

As "a protective group for a hydroxyl group, an amino group, a thiol group, an aldehyde group or a carboxyl group", it is possible to use protective groups and the like described in Protective Groups in Organic Synthesis, Third Edition, 1999, John Wiley & Sons, Inc., in which two or more functional groups may simultaneously be protected with one protective group.

Of internal alkynes, those in which one substituent ($R^2$) is an aromatic cyclic group, a substituted aromatic cyclic group, a nucleobase or a substituted nucleobase and the other substituent ($R^3$) is a halogen atom, an alkyl group, a substituted alkyl group, an aromatic cyclic group, a substituted aromatic cyclic group, a nucleobase, a substituted nucleobase, an alkoxycarbonyl group or a substituted alkoxycarbonyl group (more specifically, internal alkynes represented by general formula [5]) are preferable in order to regioselectively develop a desired reaction, and additionally, suitable for production of an optically active fluorine-containing oxeten.

As "a transition metal complex that has an optically active ligand", it is possible to cite: "a divalent cationic transition metal complex that has an optically active ligand" represented by general formula [7]; a BINOL-Ti complex represented by general formula [8]; and the like.

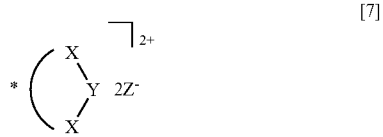

[In the formula [7], "X—*—X" represents an optically active SEGPHOS derivative (Formula (A)), an optically active BINAP derivative (Formula (B)), an optically active BIPHEP derivative (Formula (C)), an optically active P-Phos derivative (Formula (D)), an optically active PhanePhos derivative (Formula (E)), an optically active 1,4-Et$_2$-cyclo-C$_6$H$_8$-NUPHOS (Formula (F)), an optically active BOX derivative (Formula (G)) or the like. "Y" represents Ni, Pd, Pt or Cu. "Z" represents SbF$_6$, ClO$_4$, BF$_4$, OTf (Tf; CF$_3$SO$_2$), AsF$_G$, PF$_6$ or B(3,5-(CF$_3$)$_2$C$_6$H$_3$)$_4$.]

FORMULA (A)

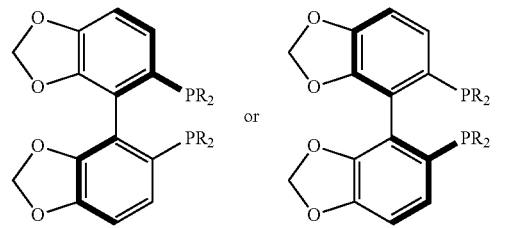

OPTICALLY ACTIVE SEGPHOS DERIVATIVE

SEGPHOS; R = C$_6$H$_5$
DM-SEGPHOS; R = 3,5-(CH$_3$)$_2$C$_6$H$_3$
DTBM-SEGPHOS; R = 4-CH$_3$O—3,5-(t-C$_4$H$_9$)$_2$C$_6$H$_2$

FORMULA (B)

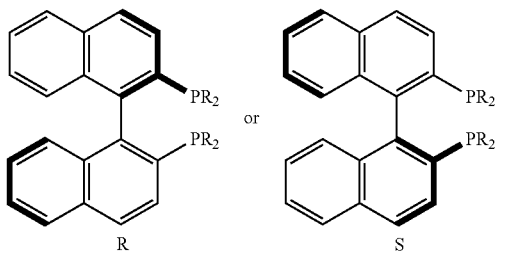

OPTICALLY ACTIVE BINAP DERIVATIVE

BINAP; R = C$_6$H$_5$
Tol-BINAP; R = 4-CH$_3$C$_6$H$_4$
Xyl-BINAP; R = 3,5-(CH$_3$)$_2$C$_6$H$_3$

-continued

FORMULA (C)

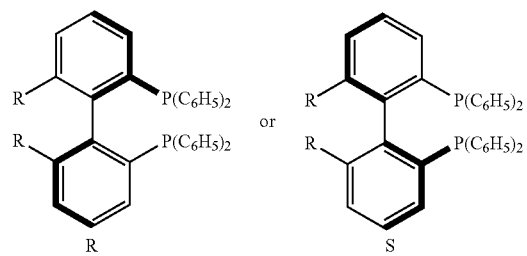

OPTICALLY ACTIVE BIPHEP DERIVATIVE

BIPHEP; R = H
BIPHEMP; R = CH$_3$
MeO-BIPHEP; R = CH$_3$O

FORMULA (D)

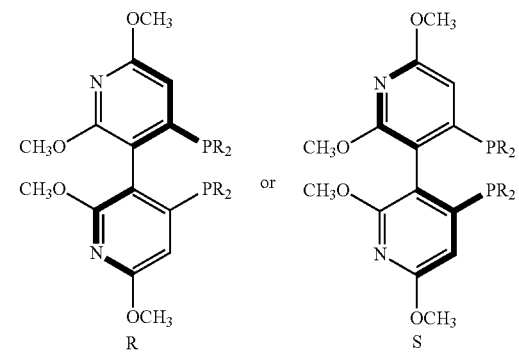

OPTICALLY ACTIVE P-Phos DERIVATIVE

P-Phos; R = C$_6$H$_5$
Tol-P-Phos; R = 4-CH$_3$C$_6$H$_4$
Xyl-P-Phos; R = 3,5-(CH$_3$)$_2$C$_6$H$_3$

FORMULA (E)

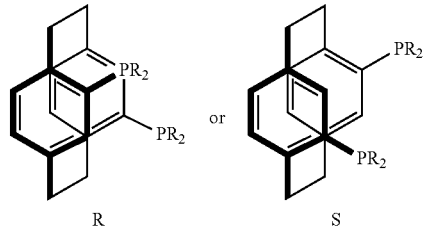

OPTICALLY ACTIVE PhanePhos DERIVATIVE

PhanePhos; R = C$_6$H$_5$
Tol-PhanePhos; R = 4-CH$_3$C$_6$H$_4$
Xyl-PhanePhos; R = 3,5-(CH$_3$)$_2$C$_6$H$_3$

FORMULA (F)

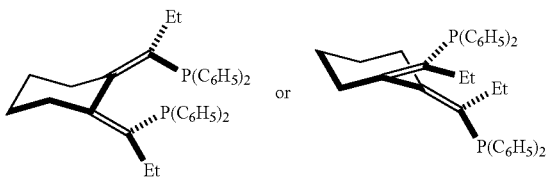

1,4-Et$_2$-cyclo-C$_6$H$_8$-NUPHOS

Et = C$_2$H$_5$

-continued

FORMULA (G)

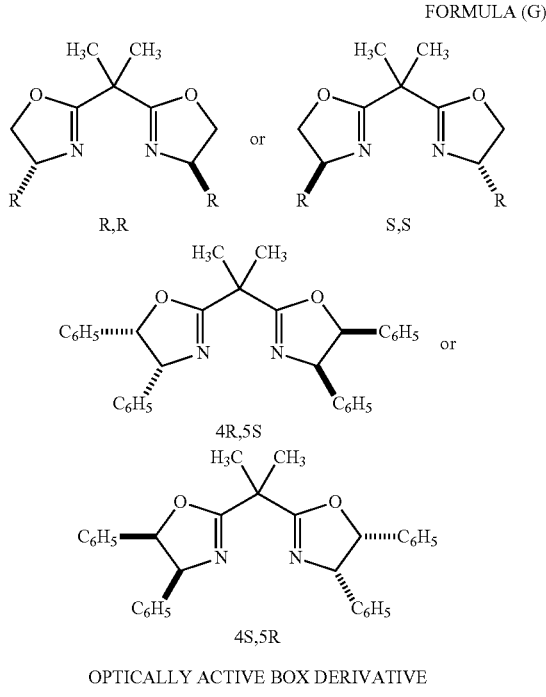

OPTICALLY ACTIVE BOX DERIVATIVE

R = i-C$_3$H$_7$
R = t-C$_4$H$_9$
R = C$_6$H$_5$

[8]

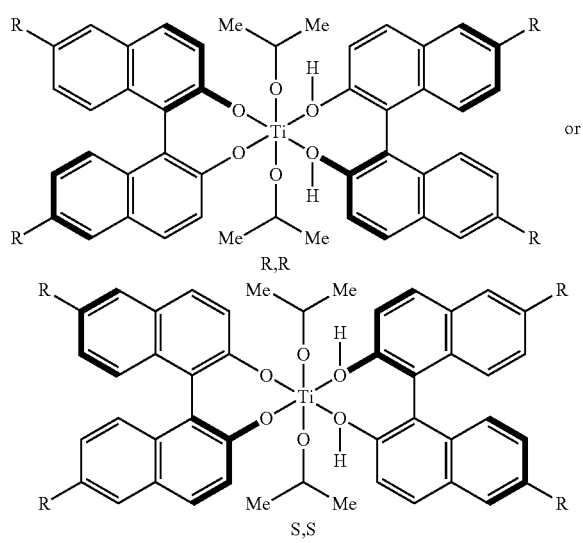

[In the formula [8], "R" represents a hydrogen atom, a chlorine atom, a bromine atom, an iodine atom or a trifluoromethyl group, and "Me" represents a methyl group.]

Of these, "a divalent cationic transition metal complex that has an optically active ligand" is preferable and "a divalent cationic palladium complex that has an optically active ligand" is particularly preferable in order to stereoselectively develop a desired reaction. Though this specification cites representative examples of the optically active ligand, it is possible to suitably use, for example, those described in CATALYTIC ASYMMETRIC SYNTHESIS, Second Edition, 2000, Wiley-VCH, Inc. Moreover, "Z" is preferably SbF$_6$, BF$_4$, OTf or B(3,5-(CF$_3$)$_2$C$_6$H$_3$)$_4$, and particularly preferably SbF$_6$, OTf or B(3,5-(CF$_3$)$_2$C$_6$H$_3$)$_4$.

These complexes can be prepared by publicly known methods, for example:
Tetrahedron Letters (England), 2004, Vol. 45, p. 183-185;
Tetrahedron: Asymmetry (England), 2004, Vol. 15, p. 3885-3889;
Angew. Chem. Int. Ed. (Germany), 2005, Vol. 44, p. 7257-7260;
J. Org. Chem. (U.S.), 2006, Vol. 71, p. 9751-9764;
J. Am. Chem. Soc. (U.S.), 1999, Vol. 121, p. 686-699; and
Nature (England), 1997, Vol. 385, p. 613-615.

Not only an isolated complex, but also a complex previously prepared in a reaction system so as not to be isolated can be used, as a matter of course. It is also possible to use one where water or an organic solvent such as acetonitrile and the like is coordinately bonded to these complexes (i.e., solvation).

Furthermore, "a cationic binuclear transition metal complex that has an optically active ligand" represented by general formula [9] may sometimes be used as well as "a divalent cationic transition metal complex that has an optically active ligand" represented by general formula [7].

[9]

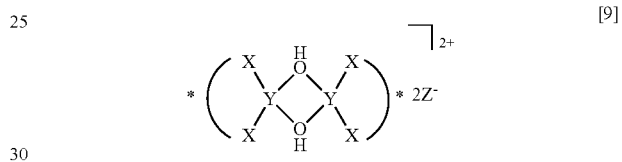

[In the formula [9], "X—*—X", "Y" and "Z" represent the same as in the general formula [7].]

The stereochemical structure of an optically active ligand [(R), (S), (R,R), (S,S) etc.] may suitably be selected according to the stereochemical structure of the target optically active fluorine-containing oxeten.

The optical purity of an optically active ligand may suitably be predetermined according to the optical purity of the target optically active fluorine-containing oxeten, and it is usually required to be not smaller than 95% e.e. (enantiomeric excess), more preferably not smaller than 97% e.e., and particularly preferably not smaller than 99% e.e.

Of these optically active ligands, BINAP derivatives are preferable, because either of its enantiomers are the most economically available and they exhibit a highly great activity when they are derivatized to an asymmetric catalyst. BINAP and Tol-BINAP are preferable and BINAP is particularly preferable.

The amount of "a transition metal complex that has an optically active ligand" to be used is required only to be not larger than 0.4 mol, more preferably 0.3 to 0.00001 mol, much more preferably 0.2 to 0.0001 mol relative to 1 mol of an internal alkyne represented by general formula [2].

Examples of a reaction solvent are: aliphatic hydrocarbons such as n-pentane, n-hexane, cyclohexane, n-heptane, etc.; aromatic hydrocarbons such as benzene, toluene, xylene, mesitylene, etc; halogenated hydrocarbons such as methylene chloride, chloroform, 1,2-dichloroethane, etc; and ethers such as diethyl ether, tert-butyl methyl ether, 1,4-dioxane, etc.

Among these, aromatic hydrocarbons, halogenated hydrocarbons and ethers are preferable and aromatic hydrocarbons and halogenated hydrocarbons are particularly preferable. These reaction solvents may be used singly or in combination.

Additionally, the production method of the present invention may be carried out in the absence of the reaction solvent.

In the case of using the reaction solvent, the amount of the reaction solvent to be used is required only to be not lower than 0.05 L, preferably 0.1 to 30 L, much more preferably 0.15 to 20 L.

The reaction temperature is required only to be within a range of from −100 to +150° C., preferably −90 to +125° C., much more preferably −80 to +100° C.

The reaction time is required only to be within a range of 48 hours. Since the reaction time differs according to a substrate, an asymmetric catalyst and reaction conditions, it is preferable to monitor the progress of the reaction by using analysis means such as gas chromatography, thin-layer chromatography, liquid chromatography, nuclear magnetic resonance (NMR) and the like thereby defining a point at which a substrate almost disappears as a termination.

intermediate for pharmaceuticals and agrochemicals. Incidentally, an optically active fluorine-containing oxeten represented by general formula [6] can be obtained through a reaction between a fluorine-containing α-ketoester represented by general formula [4] and an internal alkyne represented by general formula [5].

Referring to the 5th edition of Jikken Kagaku Koza, The Chemical Society of Japan (Maruzen) etc., an optically active fluorine-containing oxeten can be committed to a conversion reaction common in organic synthesis.

In fact, by performing hydrogenation, hydrogenolysis, acid hydrolysis or heating, an optically active fluorine-containing oxeten obtained through Examples as discussed below was converted into various useful intermediates with good yield (see Scheme 1).

SCHEME 1

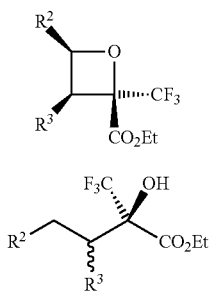
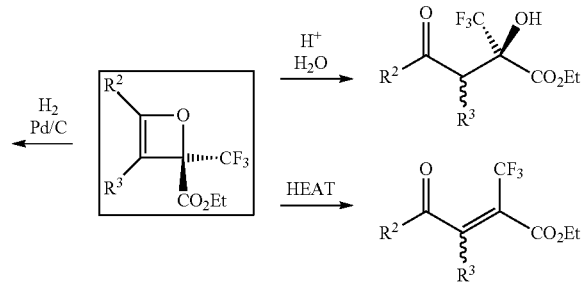

When an operation common in organic synthesis is conducted on a reaction-terminated liquid as a post-treatment, it becomes possible to obtain the target, i.e., an optically active fluorine-containing oxeten represented by general formula [3]. More specifically, by removing an asymmetric catalyst contained in the reaction-terminated liquid by a short column and then concentrating a filtered rinsed liquid, it is possible to obtain a crude product through a relatively convenient operation. The crude product may be purified with high purity as necessary, by an operation such as activated carbon treatment, distillation, recrystallization, column chromatography and the like.

The optically active fluorine-containing oxeten to be obtained by the present invention is a novel compound which may serve as an important intermediate for pharmaceuticals and agrochemicals. Among optically active fluorine-containing oxetens represented by general formula [3], preferable ones are optically active fluorine-containing oxetens in which: a perfluoroalkyl group is a trifluoromethyl group; an alkyl group of the ester moiety is a methyl group or an ethyl group; one substituent disposed on the side of an internal alkene moiety (the side of a carbon atom to which an oxygen atom is bonded) is an aromatic cyclic group, a substituted aromatic cyclic group, a nucleobase or a substituted nucleobase; and the other substituent (disposed on the side of a carbon atom to which a carbon atom is bonded) is a halogen atom, an alkyl group, a substituted alkyl group, an aromatic cyclic group, a substituted aromatic cyclic group, a nucleobase, a substituted nucleobase, an alkoxycarbonyl group or a substituted alkoxycarbonyl group (and more specifically, the preferable ones are optically active fluorine-containing oxetens represented by general formula [6]). These can be produced on a large scale and become a particularly important

EXAMPLES

Hereinafter the embodiments of the present invention will specifically be explained with reference to examples; however, the present invention is not limited by these examples.

Example 1

Under argon atmosphere, 8.0 mg (0.010 mmol) of (S)-BINAP-PdCl$_2$ represented by the following formula:

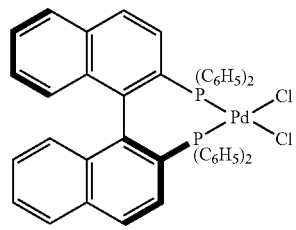

and 7.6 mg (0.022 mmol) of AgSbF$_6$ were added to 1.0 mL of methylene chloride and then stirred for 30 minutes at room temperature (by which "a divalent cationic transition metal complex that has an optically active ligand and represented by general formula [7]" where "X—*—X" represents (S)-BINAP, "Y" represents Pd and "Z" represents SbF$_6$ was produced in a reaction system).

To this asymmetric catalyst solution, 680 mg (4.0 mmol) of a fluorine-containing α-ketoester represented by the following formula:

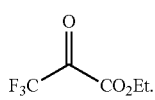

and 376 mg (2.0 mmol) of an internal alkyne represented by the following formula:

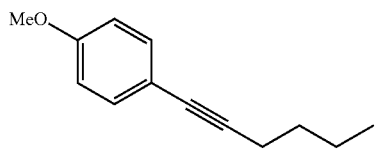

were added at −40° C., followed by 12 hours of stirring at −20° C.

A reaction-terminated liquid was directly supplied to a short column (silica gel/ethyl acetate:n-hexane=1:3) to remove "a divalent cationic transition metal complex that has an optically active ligand" and then a filtered rinsed liquid was concentrated under a reduced pressure. A residue (a crude product) was purified by column chromatography (silica gel/ethyl acetate:n-hexane=1:20) thereby obtaining 709 mg of an optically active fluorine-containing oxeten (a pure product) represented by the following formula.

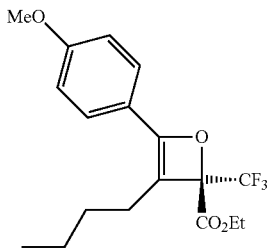

The yield was 99%. The optical purity was confirmed by chiral liquid chromatography to be 98% e.e. (R configuration).

Measurement conditions in chiral liquid chromatography are shown below.

| Column; | CHIRALPAK AD-3 |
|---|---|
| Mobile Phase; | 2-propanol:n-hexane = 1:99 |
| Flow Velocity; | 0.5 mL/min |
| Temperature; | 15° C. |
| Detector; | UV 254 nm |
| Retention Time; | Miner isomer (S configuration) 16.2 min |
| | Major isomer (R configuration) 17.7 min |

$^1$H, $^{13}$C and $^{19}$F-NMR are shown as follows.

$^1$H-NMR (300 MHz, CDCl$_3$) δ 0.93 (t, J=7.5 Hz, 3H), 1.34 (t, J=7.2 Hz, 3H), 1.33-1.60 (m, 4H), 2.43 (t, J=8.1 Hz, 2H), 3.81 (s, 3H), 4.35 (q, J=7.2 Hz, 2H), 6.92 (d, J=9.0 Hz, 2H), 7.46 (t, J=9.0 Hz, 2H).

$^{13}$C-NMR (75 MHz, CDCl$_3$) δ 13.7, 13.9, 22.5, 24.1, 30.2, 55.3, 62.6, 86.2 (q, J$_{C-F}$=33.2 Hz), 113.5, 114.1, 121.3, 122.2 (q, J$_{C-F}$=280.4 Hz), 127.8, 160.9, 162.7, 164.0.

$^{19}$F-NMR (282 MHz, CDCl$_3$) δ −75.9.

Examples 2 to 8

Example 1 was referred to in order to implement Examples 2 to 8.

The results of Examples 1 to 8 are summarized in Table 1.

TABLE 1

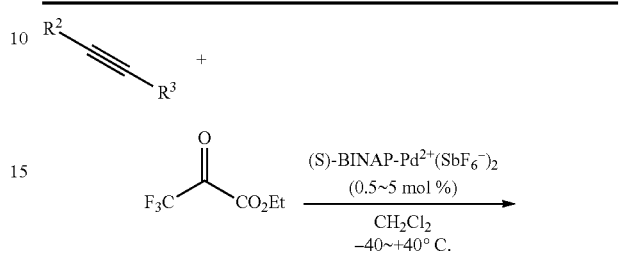

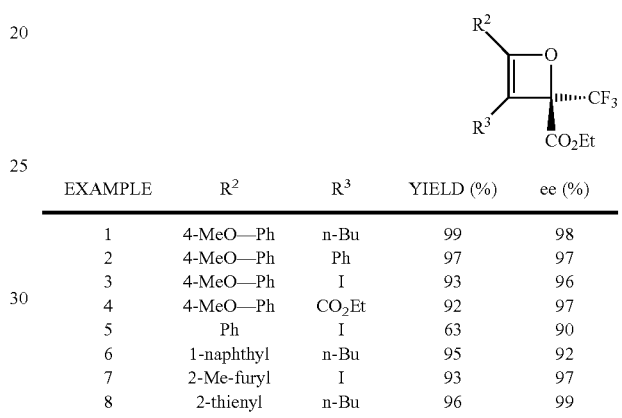

| EXAMPLE | R$^2$ | R$^3$ | YIELD (%) | ee (%) |
|---|---|---|---|---|
| 1 | 4-MeO—Ph | n-Bu | 99 | 98 |
| 2 | 4-MeO—Ph | Ph | 97 | 97 |
| 3 | 4-MeO—Ph | I | 93 | 96 |
| 4 | 4-MeO—Ph | CO$_2$Et | 92 | 97 |
| 5 | Ph | I | 63 | 90 |
| 6 | 1-naphthyl | n-Bu | 95 | 92 |
| 7 | 2-Me-furyl | I | 93 | 97 |
| 8 | 2-thienyl | n-Bu | 96 | 99 |

INDUSTRIAL APPLICABILITY

An optically active fluorine-containing oxeten produced according to the present invention can be utilized as an important intermediate for pharmaceuticals and agrochemicals.

The invention claimed is:

1. A method for producing an optically active fluorine-containing oxeten represented by general formula [3], comprising the steps of: of reacting a fluorine-containing α-ketoester of formula [1] with an internal alkyne represented by general formula [2] in the presence of a transition metal complex that has an optically active ligand,

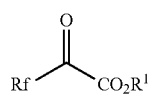

[1]

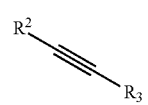

[2]

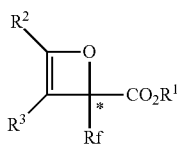

[3]

wherein Rf represents a perfluoroalkyl group and $R^1$ represents an alkyl group, wherein $R^2$ and $R^3$ mutually independently represent a halogen atom, an alkyl group, a substituted alkyl group, an aromatic cyclic group, a substituted aromatic cyclic group, a nucleobase, a substituted nucleobase, an alkoxycarbonyl group or a substituted alkoxycarbonyl group, and wherein "*" represents an asymmetric carbon.

2. A method for producing an optically active fluorine-containing oxeten represented by general formula [6], comprising the steps of: of reacting a fluorine-containing α-ketoester of formula [4] with an internal alkyne represented by general formula [5] in the presence of a divalent cationic transition metal complex that has an optically active ligand,

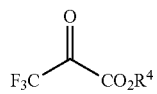

[4]

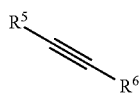

[5]

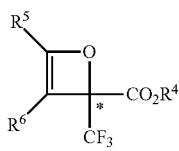

[6]

wherein $R^4$ represents a methyl group or an ethyl group,
wherein $R^5$ represents an aromatic cyclic group, a substituted aromatic cyclic group, a nucleobase or a substituted nucleobase, and $R^6$ represents a halogen atom, an alkyl group, a substituted alkyl group, an aromatic cyclic group, a substituted aromatic cyclic group, a nucleobase, a substituted nucleobase, an alkoxycarbonyl group or a substituted alkoxycarbonyl group, and wherein "*" represents an asymmetric carbon.

3. A method as claimed in claim 1, wherein the transition metal complex that has an optically active ligand is a divalent cationic palladium complex that has an optically active ligand.

4. An optically active fluoring-containing oxeten Represented by general formula [3],

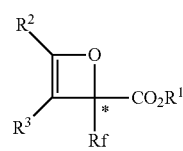

[3]

Rf represents a perfluoroalkyl group, $R^1$ represents an alkyl group, $R^2$ and $R^3$ mutually independently represent a halogen atom, an alkyl group, a substituted alkyl group, an aromatic cyclic group, a substituted aromatic cyclic group, a nucleobase, a substituted nucleobase, an alkoxycarbonyl group or a substituted alkoxycarbonyl group, and "*" represents an asymmetric carbon.

5. An optically active fluorine-containing oxeten represented by general formula [6],

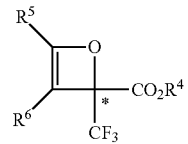

[6]

wherein $R^4$ represents a methyl group or an ethyl group, $R^5$ represents an aromatic cyclic group, a substituted aromatic cyclic group, a nucleobase or a substituted nucleobase, $R^6$ represents a halogen atom, an alkyl group, a substituted alkyl group, an aromatic cyclic group, a substituted aromatic cyclic group, a nucleobase, a substituted nucleobase, an alkoxycarbonyl group or a substituted alkoxycarbonyl group, and "*" represents an asymmetric carbon.

* * * * *

UNITED STATES PATENT AND TRADEMARK OFFICE
CERTIFICATE OF CORRECTION

| | | |
|---|---|---|
| PATENT NO. | : 8,859,789 B2 | Page 1 of 1 |
| APPLICATION NO. | : 13/989662 | |
| DATED | : October 14, 2014 | |
| INVENTOR(S) | : Koichi Mikami et al. | |

It is certified that error appears in the above-identified patent and that said Letters Patent is hereby corrected as shown below:

On the title page, column 1, item (73) should read:

Assignee: Tokyo Institute of Technology, Tokyo (JP); Central Glass Company, Limited, Ube-shi (JP)

Signed and Sealed this
Twenty-fourth Day of February, 2015

Michelle K. Lee
*Deputy Director of the United States Patent and Trademark Office*